US00PP36437P2

(12) United States Plant Patent
Zlesak et al.

(10) Patent No.: US PP36,437 P2
(45) Date of Patent: Feb. 11, 2025

(54) ***HYDRANGEA* PLANT NAMED 'BAIadele'**

(50) Latin Name: *Hydrangea arborescens*
Varietal Denomination: BAIadele

(71) Applicant: Bailey Nurseries, Saint Paul, MN (US)

(72) Inventors: David Charles Zlesak, River Falls, WI (US); Gail Katherine Soens, Woodbury, MN (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 18/754,279

(22) Filed: Jun. 26, 2024

Related U.S. Application Data

(60) Provisional application No. 63/524,191, filed on Jun. 29, 2023.

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Penny J. Aguirre

(57) ABSTRACT

A new cultivar of *Hydrangea arborescens* plant named 'BAIadele' that is characterized by its strong, stiff branches that are resistant to lodging, its compact and dense plant habit, its reblooming from midsummer through autumn, its mophead inflorescences with large sterile flowers that are dark pink in color, and its thick, dark green foliage.

3 Drawing Sheets

Botanical classification: *Hydrangea arborescens*.
Varietal denomination: 'BAIadele'.

BACKGROUND OF THE INVENTION

The present invention relates to a new and distinct cultivar of *Hydrangea arborescens* and will be referred to hereafter by its cultivar name, 'BAIadele'. 'BAIadele' represents a new smooth *Hydrangea*, a perennial shrub grown for landscape use.

'BAIadele' was derived from an ongoing breeding program by the Inventors in Cottage Grove, Minnesota. The goal of the breeding program is to create new cultivars of *Hydrangea* with strong stems, resistance to foliar diseases, reblooming, and pink flowers. 'BAIadele' originated from open-pollination of unpatented and unnamed proprietary plants of *Hydrangea arborescens* from the Inventors' breeding program. The exact parents are therefore unknown. The new cultivar was selected as a single unique plant from amongst the resulting seedlings in summer of 2017.

Asexual propagation of the new cultivar was first accomplished by softwood stem cuttings by one of the Inventors in summer of 2017 in Cottage Grove, Minnesota. Asexual propagation by softwood, semi-hardwood, and hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'BAIadele' as a unique cultivar of *Hydrangea arborescens*.

1. 'BAIadele' exhibits strong, stiff branches that are resistant to lodging.
2. 'BAIadele' exhibits a compact and dense plant habit.

3. 'BAIadele' exhibits reblooming from midsummer through autumn.
4. 'BAIadele' exhibits mophead inflorescences with large sterile flowers that are dark pink in color.
5. 'BAIadele' exhibits thick, dark green foliage.

'BAIadele' can be most closely compared to *Hydrangea arborescens* cultivars 'NCHA7' (U.S. Plant Pat. No. 30,358) and 'NCHA3' (U.S. Plant Pat. No. 28,317). 'NCHA7' is similar to 'BAIadele' in having strong, stiff branches and sterile flowers that are dark pink in color. 'NCHA7' differs from 'BAIadele' in having a less vigorous plant habit, less branching, smaller sterile flowers with sepals that are darker pink in color on the lower surface compared to the upper surface, shorter petioles, and larger leaf margin serrations. 'NCHA3' is similar to 'BAIadele' in having a compact plant habit and sterile flowers that are dark pink in color. 'NCHA3' differs from 'BAIadele' in having smaller sterile flowers with sepals that are darker pink in color on the lower surface compared to the upper surface, and thinner stems.

BRIEF DESCRIPTION OF THE DRAWINGS

The accompanying color photographs illustrate the overall appearance and distinct characteristics of the new *Hydrangea*. The photographs were taken of a plant one year in age as grown outdoors in a 2-gallon container in Cottage Grove, Minnesota.

The photograph in FIG. 1 provides a view of the plant habit of 'BAIadele' in bloom.

Figure 1:
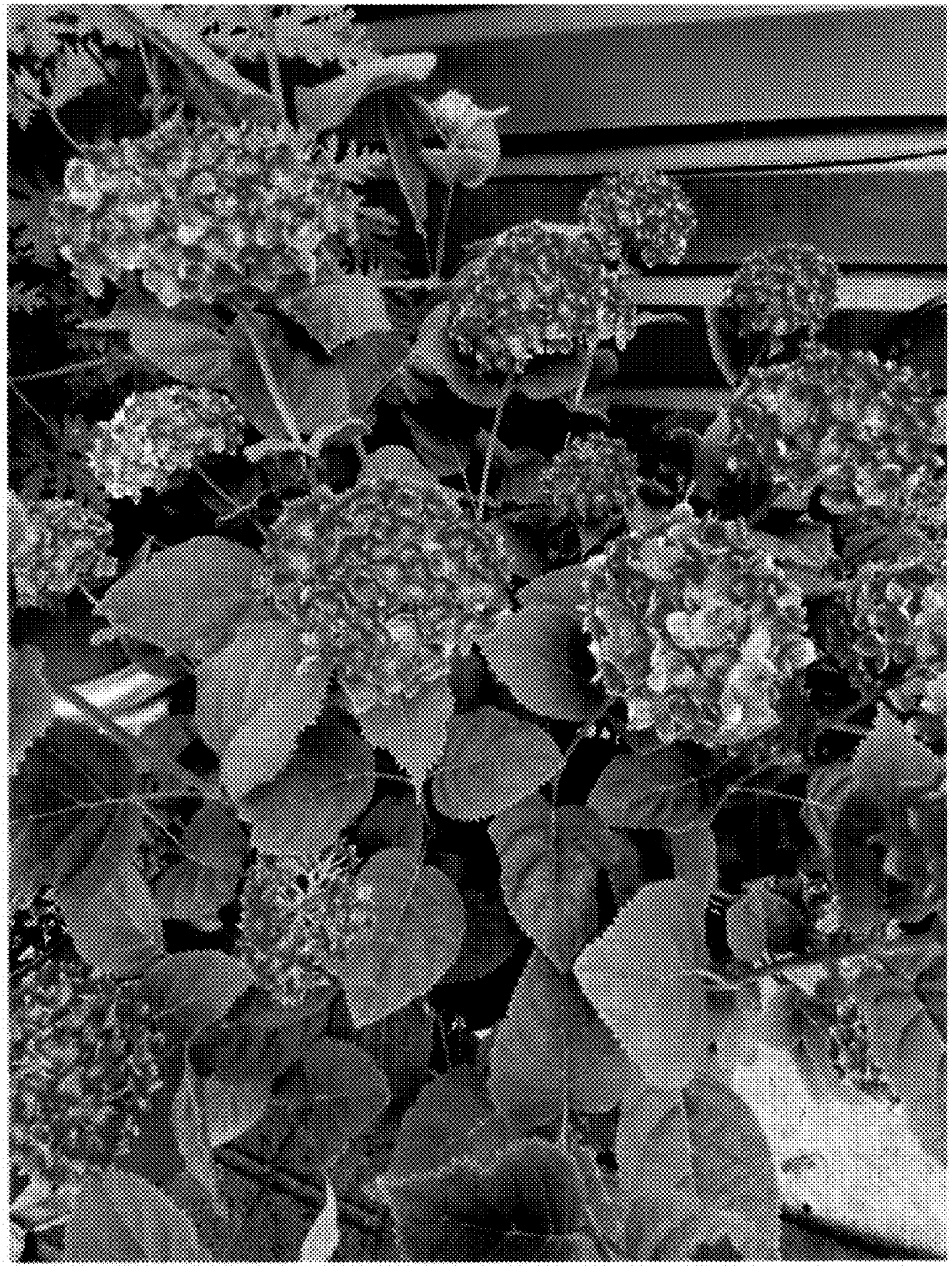
Figure 2:
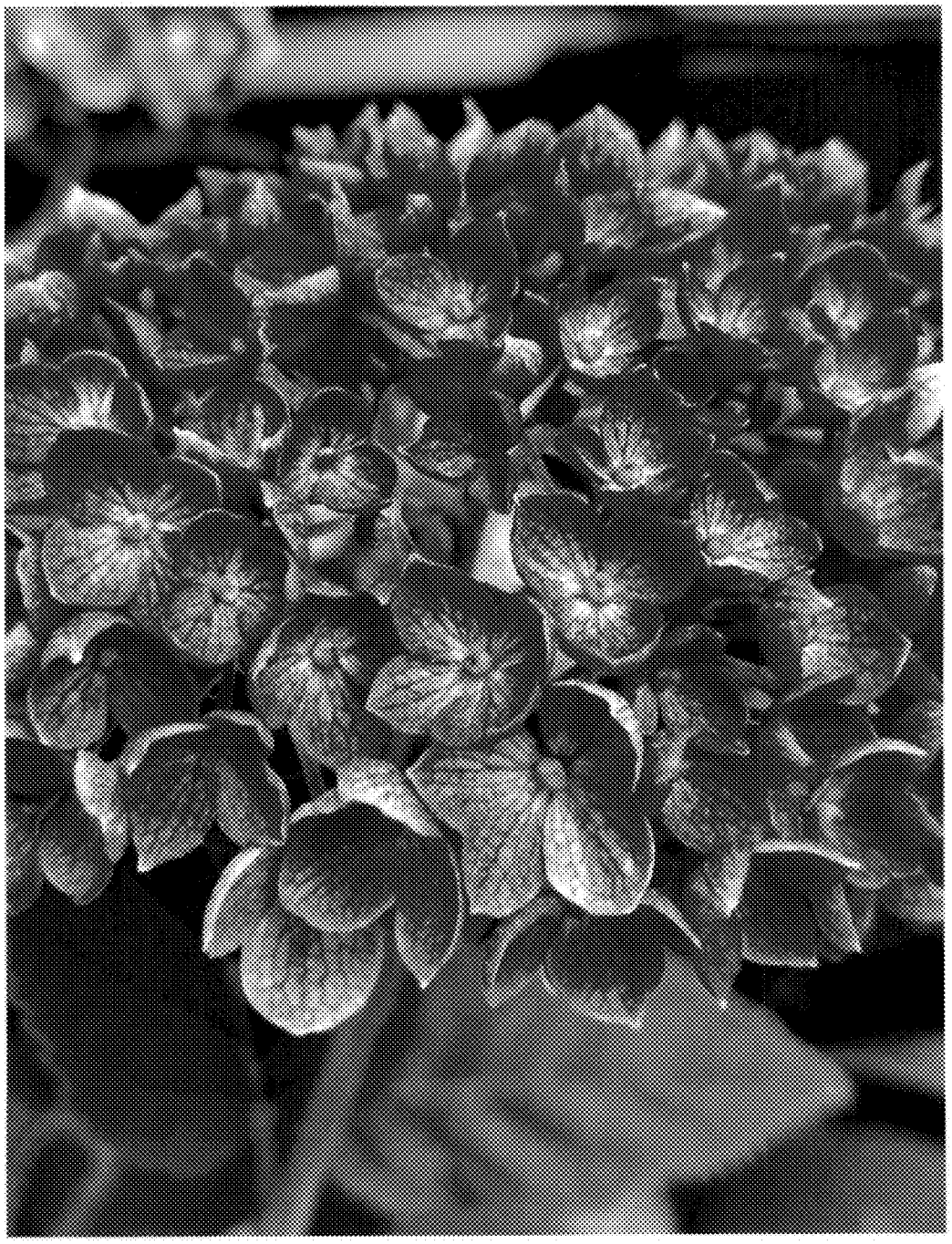

The photograph in FIG. 2 provides a close-up view of an inflorescences of 'BAIadele'.

Figure 3:
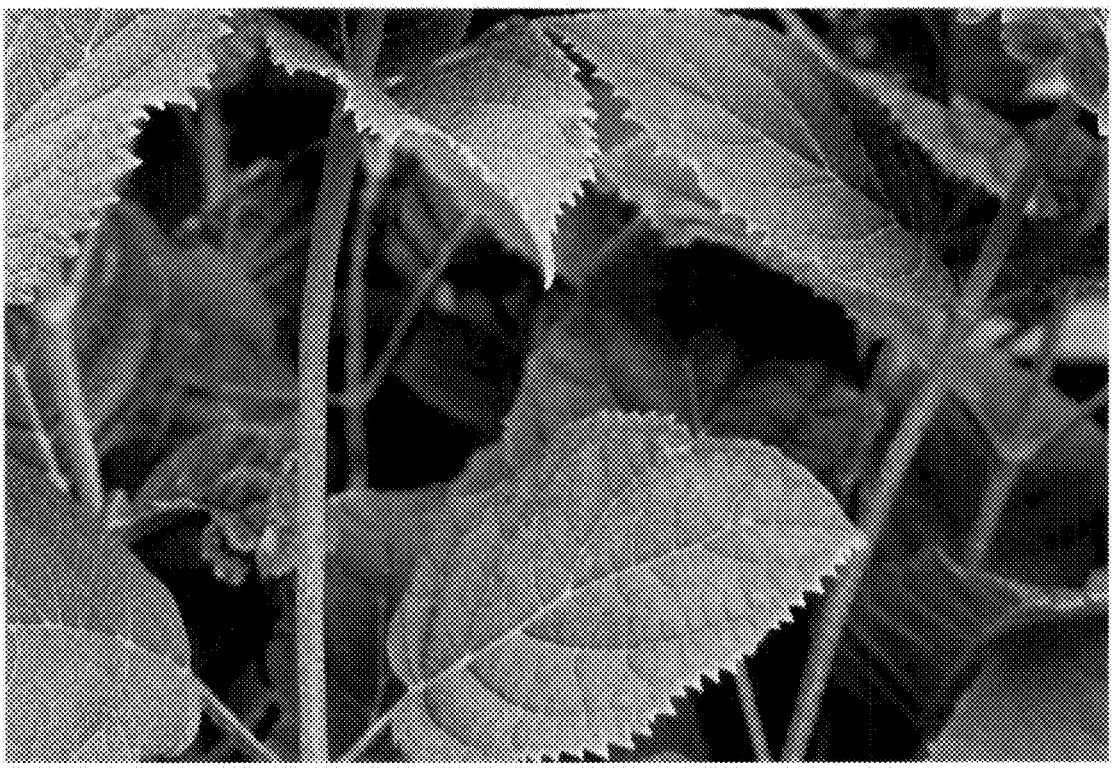

The photograph in FIG. 3 provides a close-up view of the foliage of 'BAIadele'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of plants one year old in age as grown outdoors in in 2-gallon containers in Cottage Grove, Minnesota. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—From mid to late June through mid-July and continues to rebloom until frost in Minnesota.

*Plant type.*—Perennial shrub with mophead-like flowerheads.

*Plant habit.*—Compact and rounded with strong, stiff stems.

*Height and spread.*—Average of 57 cm in height, 77 cm in width as grown in a 2-gallon container, reaches an average if 76 cm in height and 91 cm in width when grown in the landscape.

*Cold hardiness.*—At least to U.S.D.A. Zone 4.

*Diseases and pests.*—Resistance has been observed to bacterial leaf spot caused by *Xanthomonas campestris*, and 'BAIadele', like all other smooth *Hydrangea* in general, is susceptible to flea beetle (*Systena frontalis*) feeding.

*Root description.*—Fibrous.

*Time required for root development.*—20 days for root initiation, 6 weeks to produce a fully rooted young plant.

*Growth rate.*—Moderate.

Stem description:

*Stem shape.*—Rounded to slightly quadrangular.

*Stem strength.*—Strong.

*Stem aspect.*—Upright to outward.

*Stem color.*—Young and mature; 142A and 142C, flushed with 183A and 177A, older bark; 197A and 197C.

*Stem size.*—Main stems; 50 cm in length, 6 mm in diameter, lateral stems; an average of 40 cm (excluding the inflorescence) in length and 3 mm in diameter.

*Stem surface.*—Young; both surfaces dull and densely tomentose with soft matted hairs, slightly translucent and matches surface colors, too small to measure size, mature; dull, some areas smooth to slightly exfoliating.

*Branching.*—Freely branched, 3 main stems with an average of 34 lateral branches per plant.

*Internode length.*—An average of 10 cm.

Foliage description:

*Leaf shape.*—Ovate.

*Leaf arrangement.*—Opposite.

*Leaf division.*—Simple.

*Leaf number.*—An average of 8 per lateral branch.

*Leaf base.*—Cordate.

*Leaf apex.*—Acute.

*Leaf margins.*—Serrate.

*Leaf venation.*—Pinnate, upper surface slightly translucent and 150B in color, lower surface 145C, densely tomentose with soft matted hairs that match leaf surface and too small to measure size.

*Leaf size.*—An average of 9 cm in length, 6 cm in width.

*Leaf attachment.*—Petiolate.

*Leaf surface.*—Upper surface; dull and slightly rugose, lower surface; moderately rugose, upper surface moderately covered with short stiff hairs, 0.3 mm in length, NN155D in color, lower surface densely tomentose with soft matted hairs that match leaf surface and too small to measure size.

*Leaf color.*—Young and mature; upper surface 137A, lower surface 138B.

*Petioles.*—An average of 4 cm in length, 3 mm in diameter, color; 142A and 142C, flushed with 183A and 177A, both surfaces dull and densely tomentose with soft matted hairs that match surface colors and too small to measure size.

Inflorescence description:

*Inflorescence type.*—Round, slightly flattened, mophead, compound corymb of rotate-shaped sterile flowers.

*Lastingness of inflorescence.*—Sterile and fertile flowers; an average of 4 weeks in color, sterile flowers persistent, fertile flowers self-cleaning.

*Inflorescence number.*—One per lateral and main stem.

*Inflorescence size.*—An average of 5 cm in depth and 10 cm in diameter.

*Flower number.*—An average of 280 sterile flowers and 150 fertile flower buds per inflorescence.

*Flower fragrance.*—None.

*Flower aspect.*—Sterile flowers; upright, outwards and slightly drooping, fertile flowers; upright.

*Flower size.*—Sterile flowers; an average of 1.5 cm in diameter and 6 mm in depth, fertile flowers; an average of 1 cm in diameter and 5 mm in depth.

*Flower shape.*—Sterile flowers; rotate, fertile flowers; rotate.

*Flower buds.*—Sterile flowers; 4 mm in diameter, 3 mm in depth, rounded and flattened, color; 183A and 185A, fertile flowers; 1 mm in diameter, 2 mm in depth, rounded and flattened, color; 183A and 185A.

*Peduncles.*—An average of 5 cm in length and 3 mm in diameter, held upright and slightly curved, moderately strong and bendable, 142B in color, both surfaces dull and densely tomentose with soft matted hairs that match surface color, too small to measure size.

*Pedicels.*—Sterile and fertile flowers; An average of 4 mm in length and 1 mm in diameter, held upright and outward in multiple angles, moderately strong and bendable, color; 142B, sometimes flushed with 183A and 177A, both surfaces dull and densely tomentose with soft matted hairs that match surface color and too small to measure size.

*Petals.*—Sterile flowers; 3 to 4, 1.25 mm in length, 0.8 mm in width, color; young 63B, mature NN155A, ovate in shape, cuneate base, entire margins, glabrous surface, fertile flowers; 5, 2.5 mm in length, 1.5 mm in width, color: young 63C, mature NN155C, ovate in shape, cuneate base, entire margins, glabrous surface.

*Sepals*.—Sterile flowers; 4 to 5, rotate and strongly overlapping in arrangement, concave, very acute apex, cuneate base, entire margins, an average of 1 cm in length and 6 mm in width, color; upper and lower surface when opening a blend of N186D and 186A, upper and lower surface when fully open 186C, flushed with 187D, both surfaces; glabrous, smooth, velvety, fertile flowers; 5, rotate in arrangement, angled upward, flat, deltoid in shape, truncate base, acute apex, entire margins, an average of 1.5 mm in length and width, color: upper and lower surface when opening 60C, matures to 60D on both surfaces.

Reproductive organs:

*Gynoecium*.—Sterile; perigynous and underdeveloped without clear distinctions of the stigma, style, and ovary, an average of 1.5 mm in length, 1 mm in width, generally oval in shape, 155C in color, fertile flowers; perigynous, compound pistil with two carpels per flower, an average of 2.5 mm in length, stigmas separate and club-shaped 1.5 mm in length, 1 mm in diameter, angled outward from each other, 155C in color, style; 0.5 mm in length and diameter, 155C in color, ovary; globular and 1.5 mm in length and width, 154D in color.

*Androecium*.—Sterile; often none observed, but periodically 5 to 7 stamens, filaments; 1 to 3 mm in length, 0.3 mm in diameter, 155C in color, anthers; 1 mm in length and width, 160C in color, pollen; moderate, NN155B in color, fertile flowers; typically 10 stamens, filaments; 2 to 4 mm in length, 0.3 mm in diameter, 155C in color, anthers; 1 mm in length and width, 160C in color, pollen; abundant and N155B in color.

*Fruit and seed*.—Capsules; generally globular in shape with persistent sepals and stigmas; 2 to 3 mm in length and width, 165A in color at maturity, seeds; abundant and small in size, 1 mm in length, 0.15 mm in width, 164A in color.

It is claimed:

1. A new and distinct cultivar of *Hydrangea* plant named 'BAIadele' substantially as herein illustrated and described.

* * * * *